(12) United States Patent
Wiederin et al.

(10) Patent No.: US 8,262,993 B2
(45) Date of Patent: Sep. 11, 2012

(54) SLIDABLE AUTOSAMPLER TRAY

(75) Inventors: Daniel R. Wiederin, Omaha, NE (US); Gary Barrett, Omaha, NE (US)

(73) Assignee: Elemental Scientific, Inc., Omaha, NE (US)

(*) Notice: Subject to any disclaimer, the term of this patent is extended or adjusted under 35 U.S.C. 154(b) by 442 days.

(21) Appl. No.: 12/644,109

(22) Filed: Dec. 22, 2009

(65) Prior Publication Data
US 2011/0146422 A1   Jun. 23, 2011

(51) Int. Cl.
*G01N 33/00* (2006.01)
*B01L 9/00* (2006.01)
*B01L 3/00* (2006.01)
*B01L 9/06* (2006.01)
*A47F 7/00* (2006.01)
*A47F 3/14* (2006.01)
*B65D 73/00* (2006.01)

(52) U.S. Cl. ......... 422/63; 422/68.1; 422/560; 422/561; 422/562; 211/13.1; 211/85.13; 211/126.15; 206/468; 73/864.91

(58) Field of Classification Search ....................... None
See application file for complete search history.

(56) References Cited

U.S. PATENT DOCUMENTS

| | | | | |
|---|---|---|---|---|
| 5,403,554 A | * | 4/1995 | Freeman | 422/501 |
| 7,201,072 B1 | * | 4/2007 | Wiederin et al. | 73/864.25 |
| 7,690,856 B2 | * | 4/2010 | Mortensen | 403/326 |

* cited by examiner

*Primary Examiner* — In Suk Bullock
*Assistant Examiner* — Jennifer Wecker
(74) *Attorney, Agent, or Firm* — Advent IP, P.C., L.L.O.

(57) ABSTRACT

A sample tray assembly includes a first tray. The first tray defines a first slot and is disposed on a generally horizontally-oriented plane. The sample tray assembly also includes a second tray adjacent to the first tray. The second tray is configured for translational movement substantially parallel to the generally horizontally-oriented plane of the first tray between a retracted position and an extended position. The second tray defines a second slot. The second slot and the first slot are substantially aligned when the second tray is in the retracted position. The sample tray additionally includes a base member supporting the first tray. The second tray is slidably coupled with the base member.

6 Claims, 5 Drawing Sheets

SLIDABLE AUTOSAMPLER TRAY

FIELD

The present invention relates generally to laboratory instrumentation, particularly automated sampling devices for drawing samples from sample vessels, and more specifically, to an automated sampling device having a slidable tray for supporting samples.

BACKGROUND

In many laboratory settings, it is often desirable to analyze a relatively large number of chemical or biochemical samples in an approximately continuous operation, such as with limited preparation time between samples. In order to streamline such processes, the manipulation of samples has been mechanized. Such mechanized sampling is commonly referred to as autosampling and is performed using an automated sampling device or autosampler. Samples may be accessible to the autosampler by a sampling probe. Typically, samples are positioned on a moveable tray, which positions the samples for access by the sample probe, however, samples may also be positioned on a stationary tray for access by a moveable sample probe.

SUMMARY

A sample tray assembly includes a first tray. The first tray defines a first slot and is disposed on a generally horizontally-oriented plane. The sample tray assembly also includes a second tray adjacent to the first tray. The second tray is configured for translational movement substantially parallel to the generally horizontally-oriented plane of the first tray between a retracted position and an extended position. The second tray defines a second slot. The second slot and the first slot are substantially aligned when the second tray is in the retracted position. The sample tray additionally includes a base member supporting the first tray. The second tray is slidably coupled with the base member.

A sample tray assembly for an autosampler includes a support assembly for supporting a tray. The support assembly is disposed on a generally horizontally-oriented plane, and the support assembly defines a first slot. The sample tray assembly for an autosampler also includes a tray assembly slideably coupled with the support assembly for translational movement substantially parallel to the generally horizontally-oriented plane of the support assembly. The tray assembly defines a second slot, and is positionable between a retracted and an extended position. The first slot and the second slot substantially align when the tray assembly is in the retracted position.

An autosampler unit includes an arm assembly for supporting a fluid probe. The arm assembly includes a generally vertically-oriented support post and a generally horizontally-oriented fluid probe support arm. The autosampler unit also includes a first tray. The first tray defines a first slot. The autosampler unit additionally includes a second tray adjacent the first tray. The second tray is configured to slide relative to the first tray, defines a second slot, and is slidable between a retracted position and an extended position. The first slot and the second slot are substantially aligned when the second tray is in the retracted position, and the second slot is configured to receive the generally vertically-oriented support post when the second tray is transitioned from the extended position to the retracted position. The autosampler unit further includes a base member supporting the first tray. The second tray is slidably coupled with the base member.

It is to be understood that both the foregoing general description and the following detailed description are exemplary and explanatory only and are not necessarily restrictive as claimed. The accompanying drawings, which are incorporated in and constitute a part of the specification, illustrate an embodiment and together with the general description, serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the presently preferred embodiments of the disclosure, examples of which are illustrated in the accompanying drawings.

Referring to FIG. 1-5, embodiments of a slidable autosampler tray 100 are shown. The slidable autosampler tray 100 may include a support assembly 102 for supporting a first tray 104, and a tray assembly 106 slidably coupled with the support assembly 102 for translational movement. The terms "slidable" and "slidably" may be used herein to describe a configuration which enables movement of at least one portion of the slidable autosampler tray 100 with reference to at least one other portion of the slidable autosampler tray 100. For instance, the description of the tray assembly 106 being slidably coupled with the support assembly 102 for translational movement may indicate that the tray assembly 106 moves or slides relative to the support assembly 102 while being coupled together.

Figure 1:
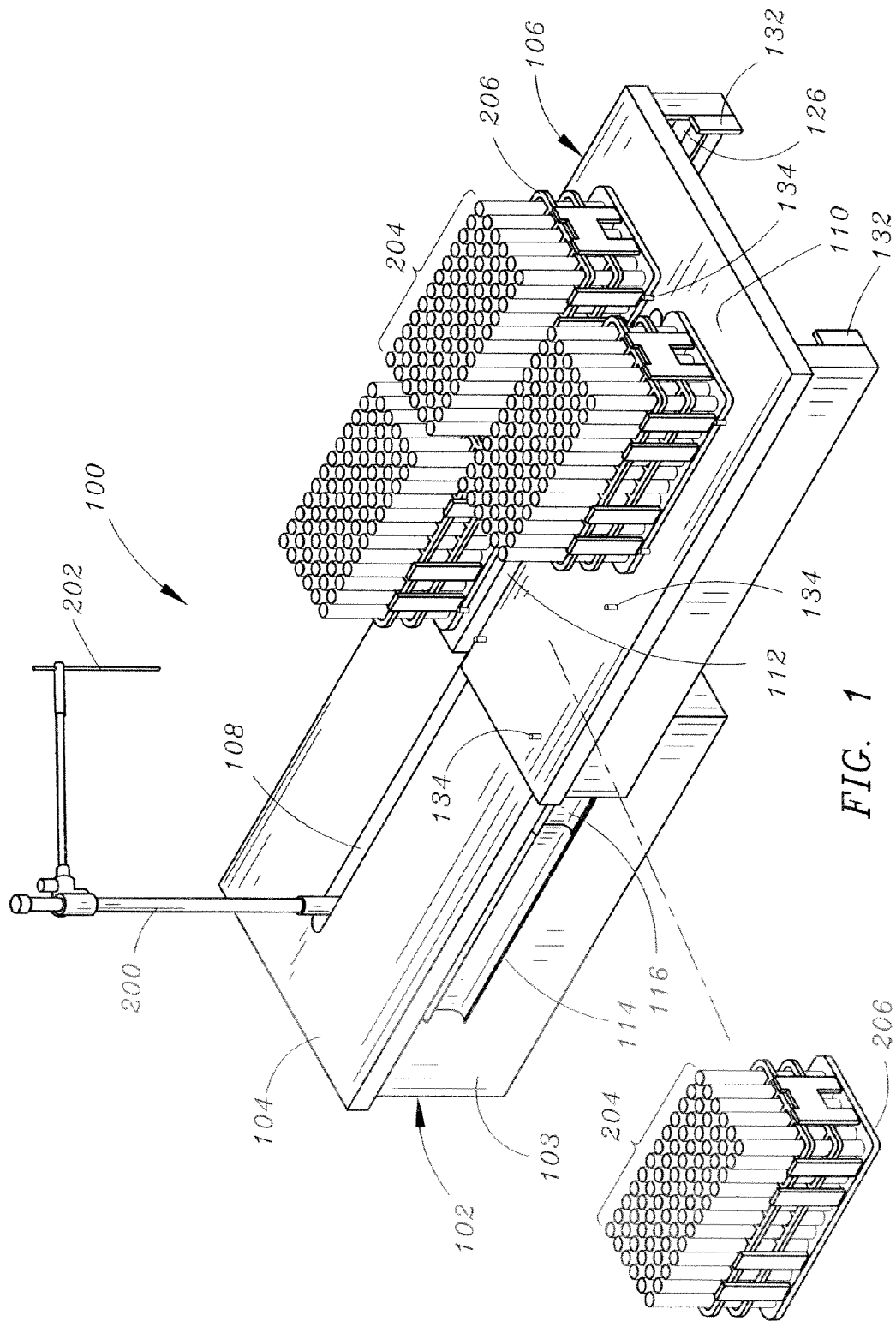
FIG. 1 is an isometric view of an embodiment of a slidable autosampler tray, shown in an extended position.
Figure 2:
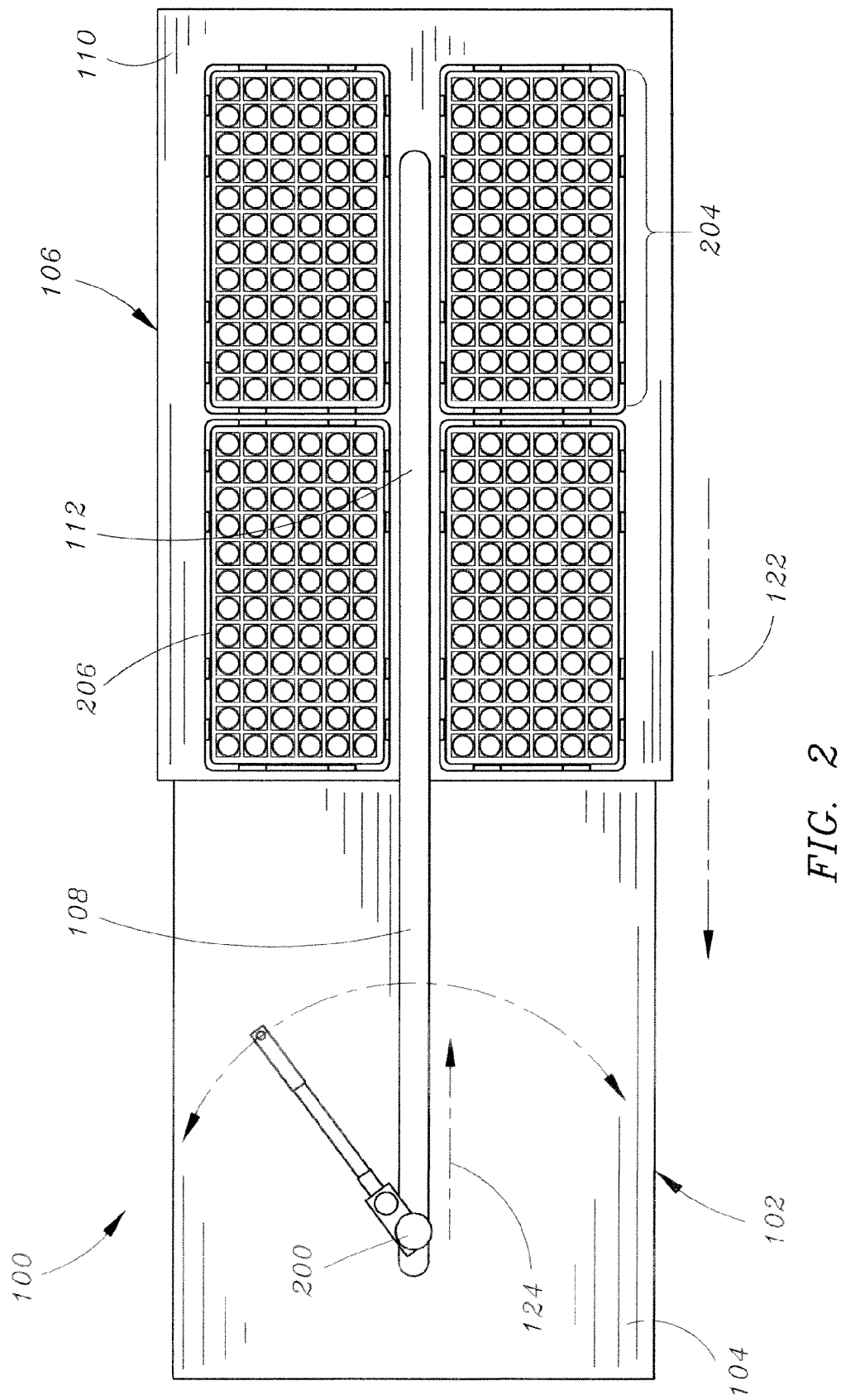
FIG. 2 is a top plan view of the slidable autosampler tray of FIG. 1, shown in the extended position.
Figure 4:
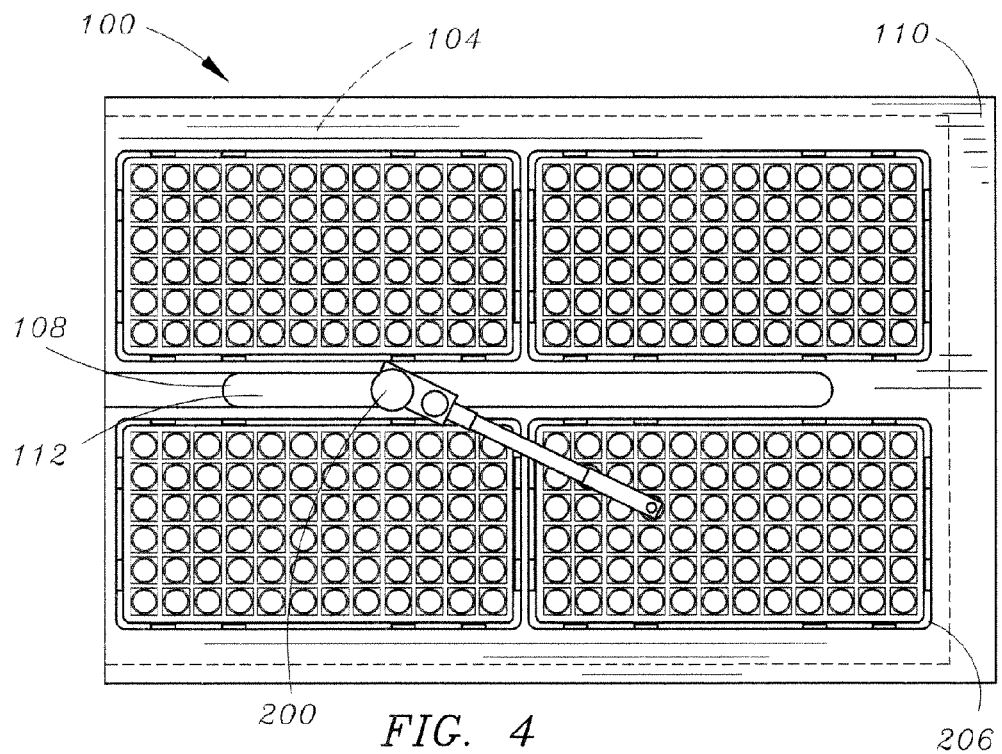
FIG. 4 is a top plan view of the slidable autosampler tray of FIG. 1, shown in the retracted position.
Figure 5:
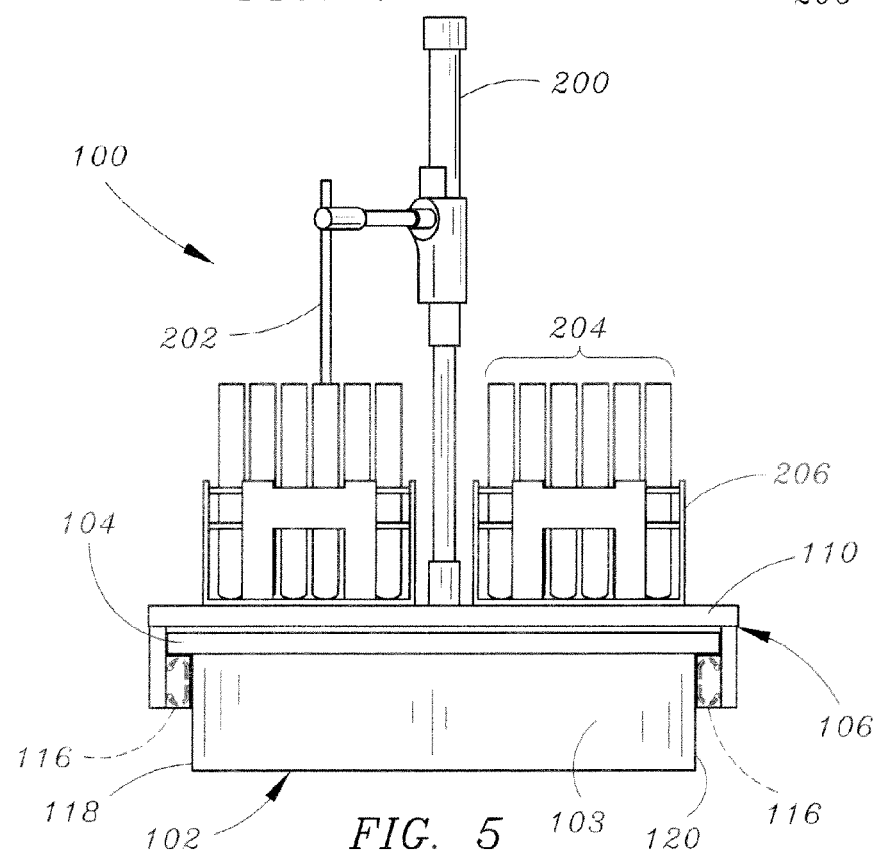
FIG. 5 is a side elevation view of the slidable autosampler tray of FIG. 4.

The support assembly 102 may define a first slot 108. The first slot 108 may be positioned longitudinally on the support assembly 102, such as shown in FIGS. 1, 2, and 4. For example, the first tray 104 may define the first slot 108 which at least partially bisects the first tray 104 and is positioned longitudinally along the first tray 104. The support assembly 102 may be disposed on a generally horizontally-oriented plane, such that the support assembly 102 may support the tray assembly 106 disposed on another generally horizontally-oriented plane, which may be located above the plane of the support assembly 102. The support assembly 102 may also include a base member 103. The base member 103 may couple with the first tray 104 to form at least a portion of the support assembly 102.

Figure 3:
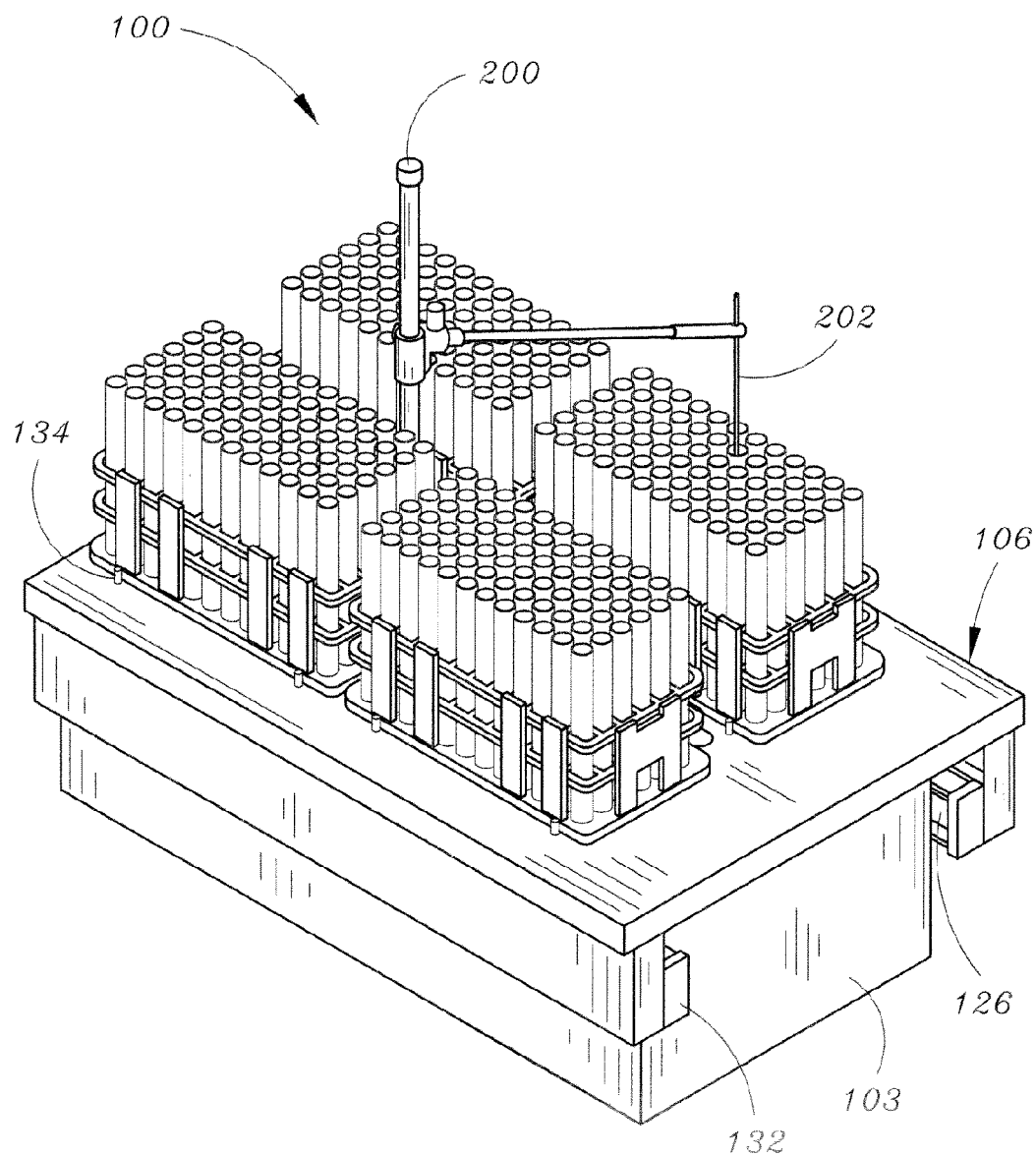
FIG. 3 is an isometric view of the slidable autosampler tray of FIG. 1, shown in a retracted position.

The tray assembly 106 may include a second tray 110 and may be slidably coupled with the support assembly 102 for translational movement substantially parallel to the generally horizontally-oriented plane of the support assembly 102. By slidably coupling the tray assembly 106 with the support assembly 102, the tray assembly 106 (including the second tray 110) may be positionable between an extended position (as shown in FIGS. 1 and 2) and a retracted position (as shown in FIGS. 3 and 4). In the extended position, the tray assembly 106 may be positioned distal the support assembly 102, such that at least a portion of the tray assembly 106 may extend beyond the support assembly 102. For example, when in the extended position, the majority of the tray assembly 106 may extend beyond the support assembly 102. In the retracted position, the tray assembly 106 may be positioned proximal the support assembly 102, such that the tray assembly 106 is positioned substantially directly above the support assembly 102.

The tray assembly 106 may also include a second slot 112. The second slot 112 may be positioned longitudinally on the tray assembly 106, such as shown in FIGS. 1, 2, and 4. For example, the second tray 110 may define the second slot 112 which at least partially bisects the second tray 110 and is positioned longitudinally along the second tray 110. The first slot 108 and the second slot 112 may substantially align when the tray assembly 106 is in the retracted position. FIG. 4 displays the substantial alignment of the first slot 108 and the second slot 112 in a top plan view. As can be seen, the tray assembly 106 is in the retracted position over the support assembly 102, and the second slot 112 is positioned above the first slot 108. For instance, when the first slot 108 and the second slot 112 are substantially aligned, a portion of the first slot 108 directly corresponds with a portion of the second 112, such that a continuous path is formed. The continuous path may enable passage of a device/article through each of the first slot 108 and the second slot 112 simultaneously. For example, as described below, when the first slot 108 and the second slot 112 are substantially aligned, a support post 200 may travel through the first slot 108 and the second slot 112 simultaneously.

The slidable autosampler tray 100 may include a rail device 114 configured to slidably couple the tray assembly 106 with the support assembly 102. The rail device 114 may include a rail 116 coupled to a first side 118 and a second side 120 of the support assembly 102. For instance, the first side 118 and the second side 120 may be opposing sides which are positioned substantially parallel to a first direction of travel 122 between the extended position and the retracted position. In one embodiment, the rail 116 is configured to retract in the first direction of travel 122 and is configured to extend in a second direction of travel 124. For example, the second direction of travel 124 may be the direction of movement of the tray assembly 106 from the retracted position to the extended position. The tray assembly 106 may include a rail track 126 configured to mate with the rail 116, such as to slidably couple the tray assembly 106 with the support assembly 102. In one embodiment, the rail track 126 is supported on the tray assembly 106 by opposing side portions 128 and 130, which may be coupled to the second tray 110. The opposing side portions 128 and 130 may each include a stop plate 132 at an end opposite the rail 116. The stop plate 132 may be configured to prevent movement of the tray assembly 106 during transition from the extended position to the retracted position once the tray assembly 106 reaches the retracted position. For instance, the stop plate 232 may prevent the tray assembly 106 from sliding off of the support assembly 102 or from contacting a support post 200 (described below).

While the slidable autosampler tray 100 is described herein as including a rail device 114 configured to slidably couple the tray assembly 106 with the support assembly 102, it may be appreciated that other means of slidably coupling the tray assembly 106 with the support assembly 102 without departing from the scope of the present disclosure. For example, other suitable methods of slidable coupling known in the art may be utilized.

The first slot 108 and the second slot 112 may be configured to permit passage of a support post 200. When the first slot 108 and the second slot 112 are substantially aligned, the support post 200 may pass through each of the first slot 108 and the second slot 112 simultaneously. The support post 200 may be a generally vertically-oriented support post configured to support a fluid probe 202 of an autosampler. The support post may rotate axially and may move longitudinally through at least one of the first slot 108 and the second slot 112. For instance, such functionality of a support post and a fluid probe may be described in U.S. Pat. No. 7,201,072, entitled "Automated sampling device," filed Oct. 15, 2004, which is hereby incorporated by reference in its entirety. The second slot 112 may also extend through a side of the tray assembly 106 (e.g., through the second tray 110). For instance, the second slot 112 may be configured to receive the support post 200, such as when the tray assembly 106 is transitioned from the extended position to the retracted position.

The second tray 110 may be configured to support a plurality of sample vessels 204. The plurality of sample vessels 204 may be arranged in and/or supported by one or more sample racks 206. For instance, the sample racks 206 may provide uniform spacing of the plurality of sample vessels 204, which may aid in sample testing by an autosampler. Additionally, the sample racks 206 may provide a stable base for the plurality of sample vessels 204, such as during translational movement of the second tray 110. The second slot 112 may provide the sample probe 202 with access to the plurality of sample vessels 204 on the second tray 110. The second tray 110 may also include one or more protrusions 134, which may be configured to guide placement of a sample rack 206 onto the second tray 110 and to at least partially hold the sample racks 206 in place during translational movement of the second tray 110. For instance, an operator may place a sample rack 206 loaded with sample vessels 204 between protrusions 134.

The tray assembly 106 may be positioned into the extended position for ease of access to the plurality of sample vessels 204 and the sample racks 206, and to isolate the support post 200. For example, an operator may position the tray assembly 106 into the extended position to isolate the support post 200 from the tray assembly, such as to provide an unencumbered work environment to perform maintenance on the support post 200 and/or the sample probe 202. Additionally, an operator may position the tray assembly 106 into the extended position to isolate the tray assembly 106 from the support post 200, such as to avoid encumbrance by the support post 200 and/or the sample probe 202, to load samples into the sample vessels 204, or to load the sample racks 206 with sample vessels 204.

Figure 6:
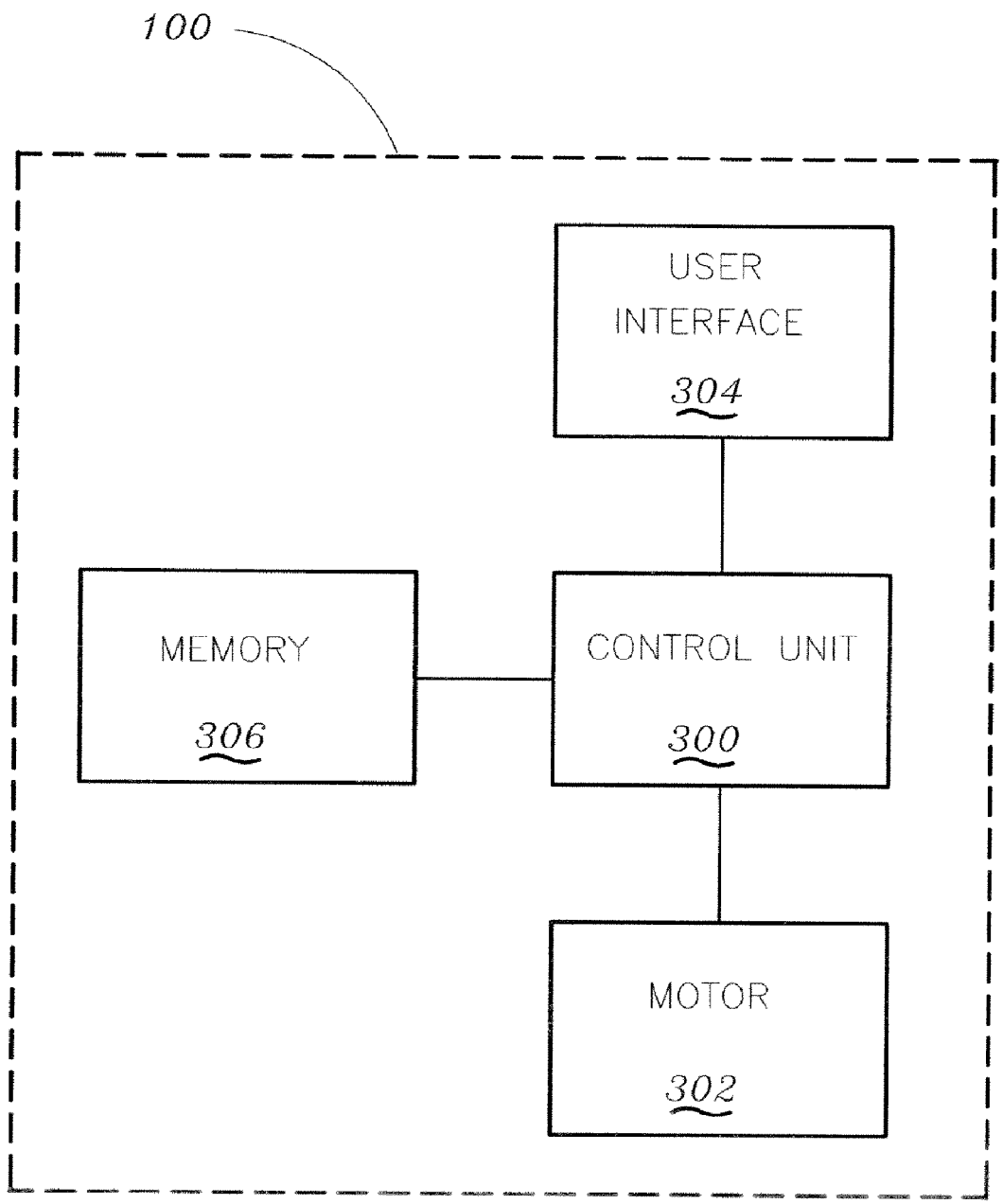
FIG. 6 is a schematic illustration of an automatic slidable autosampler tray.

Referring now to FIG. 6, it is contemplated that the movement of the tray assembly 106 between the retracted position and the extended position may be controlled automatically. The slidable autosampler tray 100 may be controlled by the controller and motor which controls movement of the support post 200 and sample probe 202, or may be controlled by a separate control unit 300 and/or motor 302. For instance, the tray assembly 106 may be automatically transitioned from the retracted position to the extended position after the sample probe 202 has engaged a batch of samples from the sample vessels 204. Thus, the second tray 110 may be positioned away from the support post 200 and the sample probe 202 for ease of access to the sample racks 206 and sample vessels 204, such as for removing used sample vessels 204 and replacing with new samples to be tested. Additionally, the control unit 300 may cause the motor 302 to move the tray assembly 106 from the extended position to the retracted position automatically, or upon interaction between an operator and a user interface 304. The control unit 300 may execute instructions (e.g., computer language programming) directed to controlling the positioning of the tray assembly 106. The instructions may be stored in a memory 306. For instance, the instructions stored in memory 306 may indicate that the control unit 300 engages the motor 302 to move the tray assembly 106 from the retracted position to the extended position after all samples scheduled to be tested have been engaged by the sample probe 202. Further, automatic movement may allow for precise control, which may prevent uncontrolled movement of the tray assembly 106 and may prevent samples from mixing between sample vessels 204, such as if the tray assembly 106 is transitioned relatively rapidly.

It is believed that the present disclosure and many of its attendant advantages will be understood by the foregoing description, and it will be apparent that various changes may be made in the form, construction and arrangement of the components thereof without departing from the scope and spirit of the disclosure or without sacrificing all of its material advantages. The form herein before described being merely an explanatory embodiment thereof, it is the intention of the following claims to encompass and include such changes.

What is claimed is:

1. An autosampler unit, comprising:
   an arm assembly for supporting a fluid probe, the arm assembly including a generally vertically-oriented support post and a generally horizontally-oriented fluid probe support arm;
   a first tray, the first tray defining a first slot;
   a second tray adjacent the first tray, the second tray configured to slide relative to the first tray, the second tray defining a second slot, the second tray slidable between a retracted position and an extended position, the first slot and the second slot are substantially aligned when the second tray is in the retracted position, the second slot configured to receive the generally vertically-oriented support post when the second tray is transitioned from the extended position to the retracted position; and
   a base member supporting the first tray, the second tray slidably coupled with the base member.

2. The autosampler unit of claim 1, wherein the first slot and the second slot are configured to provide a continuous path through which the generally vertically-oriented support post may pass.

3. The autosampler unit of claim 2, wherein the first slot and the second slot are configured to provide a continuous path through which the generally vertically-oriented support post may pass when the second tray is in the retracted position.

4. The autosampler unit of claim 1, further including:
   at least one protrusion coupled with the second tray, the at least one protrusion configured to guide placement of a sample rack onto the second tray.

5. The autosampler unit of claim 1, wherein the second slot at least partially bisects the second tray.

6. The autosampler unit of claim 1, further including:
   a rail device configured to slidably couple the second tray with the base member.

* * * * *